United States Patent [19]

Kerrigan et al.

[11] Patent Number: 5,869,492

[45] Date of Patent: Feb. 9, 1999

[54] CONDENSED THIAZOLE DERIVATIVES, HAVING 5-HT RECEPTOR AFFINITY

[75] Inventors: Frank Kerrigan; Sharon Crawford Cheetham; Roy Victor Davies, all of Nottingham, Great Britain

[73] Assignee: Knoll Aktiengesellschaft, Ludwigshafen, Germany

[21] Appl. No.: 973,960

[22] PCT Filed: Jun. 20, 1996

[86] PCT No.: PCT/EP96/02676

§ 371 Date: Dec. 15, 1997

§ 102(e) Date: Dec. 15, 1997

[87] PCT Pub. No.: WO97/02269

PCT Pub. Date: Jan. 23, 1997

[30] Foreign Application Priority Data

Jul. 1, 1995 [GB] United Kingdom .................. 9513467

[51] Int. Cl.⁶ ........................ A61K 31/495; C07D 513/06
[52] U.S. Cl. ...................... 514/258; 514/368; 544/298; 548/154
[58] Field of Search ............. 548/154; 544/278; 514/258, 368

[56] References Cited

FOREIGN PATENT DOCUMENTS

41883/78  11/1978  Australia .

*Primary Examiner*—Johann Richter
*Assistant Examiner*—Laura R. C. Lutz
*Attorney, Agent, or Firm*—Keil & Weinkauf

[57] ABSTRACT

Compounds of formula I

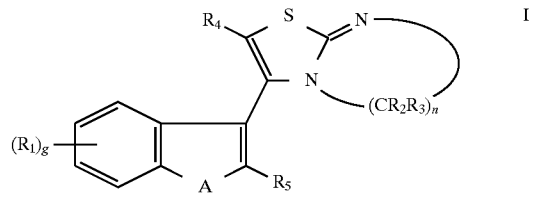

in which

A is $S(O)_p$ or O;

p is 0, 1 or 2;

g is 0, 1, 2, 3, or 4;

n is 2 or 3; and $R_1$, $R_2$, $R_3$, $R_4$ and $R_5$ are optional substituents have utility in the treatment of central nervous system disorders, for example depression, anxiety, psychoses (for example schizophrenia), tardive dyskinesia, obesity, drug addiction, drug abuse, cognitive disorders, Alzheimer's disease, senile dementia, cerebral ischemia, obsessive-compulsive behavior, panic attacks, social phobias, eating disorders and anorexia, non-insulin dependent diabetes mellitus, hyperglycemia, and stress.

11 Claims, No Drawings

CONDENSED THIAZOLE DERIVATIVES, HAVING 5-HT RECEPTOR AFFINITY

This application is a 371 of PCT/EP96/02676 filed Jun. 20, 1996.

The present invention relates to certain novel substituted dihydroimidazo[2,1-b]thiazole and dihydro-5H-thiazolo[3,2-a]pyrimidine compounds which have affinity for 5-HT$_{1A}$ receptors and which inhibit neuronal reuptake of 5-hydroxytryptamine and/or noradrenaline, to processes for their preparation, to pharmaceutical compositions containing them and to their use in the treatment of central nervous system disorders, for example depression, anxiety, psychoses (for example schizophrenia), tardive dyskinesia, obesity, drug addiction, drug abuse, cognitive disorders, Alzheimer's disease, senile dementia, cerebral ischaemia, obsessive-compulsive behaviour, panic attacks, social phobias, eating disorders and anorexia, non-insulin dependent diabetes mellitus, hyperglycaemia, and stress.

Sharpe C. J and Shadbolt R. S. disclose certain dihydroimidazo[2,1-b]thiazole compounds having antidepressant activity, Journal of Medicinal Chemistry, 1971, Vol 14 No.10, p977–982. However, the document also states that these compounds were generally less active and more toxic than the imidazolines also disclosed in the document. The compounds of the present invention are not disclosed or suggested in this document.

The present invention provides compounds of formula I

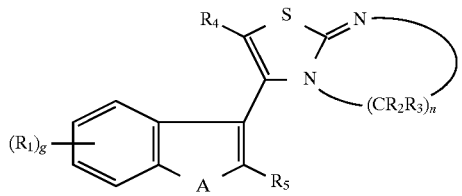

including pharmaceutically acceptable salts thereof
in which
A is S(O)$_p$ or O;
p is 0, 1 or 2;
g is 0, 1, 2, 3, or 4;
n is 2 or 3;
R$_1$ is a) halo, b) an alkyl group containing 1 to 3 carbon atoms optionally substituted by one or more halo, c) an alkoxy group containing 1 to 3 carbon atoms optionally substituted by one or more halo, d) an alkylthio group, an alkylsulphinyl group or an alkylsulphonyl group each containing 1 to 3 carbon atoms optionally substituted by one or more halo, e) hydroxy, f) an acyloxy group containing 1 to 3 carbon atoms, g) a hydroxyalkyl group containing 1 to 3 carbon atoms, h) cyano, i) an alkanoyl group containing 1 to 6 carbon atoms, j) an alkoxycarbonyl group containing 2 to 6 carbon atoms, k) a carbamoyl group or a carbamoylmethyl group each optionally N-substituted by one or two alkyl groups each containing 1 to 3 carbon atoms, l) a sulphamoyl or sulphamoylmethyl group each optionally N-substituted by one or two alkyl groups each containing 1 to 3 carbon atoms, or m) an amino group optionally substituted by one or two alkyl groups each containing 1 to 3 carbon atoms; R$_1$ being the same or different when g is 2, 3 or 4;

R$_2$, R$_3$ and R$_4$ independently are H or an alkyl group containing 1 to 3 carbon atoms optionally substituted by one or more halo; and R$_5$ is a) halo, b) an alkyl group containing 1 to 3 carbon atoms optionally substituted by one or more halo, c) an alkoxy group containing 1 to 3 carbon atoms optionally substituted by one or more halo, d) an alkylthio group, an alkylsulphinyl group or an alkylsulphonyl group each containing 1 to 3 carbon atoms optionally substituted by one or more halo, e) hydroxy, f) an acyloxy group containing 1 to 3 carbon atoms, g) a hydroxyalkyl group containing 1 to 3 carbon atoms, h) cyano, i) an alkanoyl group containing 1 to 6 carbon atoms, j) an alkoxycarbonyl group containing 2 to 6 carbon atoms, k) a carbamoyl group or a carbamoylmethyl group each optionally N-substituted by one or two alkyl groups each containing 1 to 3 carbon atoms, l) a sulphamoyl or sulphamoylmethyl group each optionally N-substituted by one or two alkyl groups each containing 1 to 3 carbon atoms, m) an amino group optionally substituted by one or two alkyl groups each containing 1 to 3 carbon atoms, or n) H.

In one group of compounds of formula I, A is S(O)$_p$ or O; p is 0, 1 or 2; g is 0, 1, 2, 3 or 4; n is 3; R$_1$ is a) halo, b) an alkyl group containing 1 to 3 carbon atoms optionally substituted by one or more halo, c) an alkoxy group containing 1 to 3 carbon atoms optionally substituted by one or more halo, d) an alkylthio group, an alkylsulphinyl group or an alkylsulphonyl group each containing 1 to 3 carbon atoms optionally substituted by one or more halo, e) hydroxy, f) an acyloxy group containing 1 to 3 carbon atoms, g) a hydroxyalkyl group containing 1 to 3 carbon atoms, h) cyano, i) an alkanoyl group containing 1 to 6 carbon atoms, j) an alkoxycarbonyl group containing 2 to 6 carbon atoms, k) a carbamoyl group or a carbamoylmethyl group each optionally N-substituted by one or two alkyl groups each containing 1 to 3 carbon atoms. l) a sulphamoyl or sulphamoylmethyl group each optionally N-substituted by one or two alkyl groups each containing 1 to 3 carbon atoms, or m) an amino group optionally substituted by one or two alkyl groups each containing 1 to 3 carbon atoms; R$_1$ being the same or different when g is 2, 3 or 4; R$_2$, R$_3$ and R$_4$ independently are H or an alkyl group containing 1 to 3 carbon atoms optionally substituted by one or more halo; and R$_5$ is H, halo, or an alkyl group containing 1 to 3 carbon atoms optionally substituted by one or more halo.

In more preferred compounds in this group, A is S(O)$_p$ or O; p is 0; g is 0 or 1; n is 3; R$_1$ is halo, an alkoxy group containing 1 to 3 carbon atoms, or cyano; and R$_2$, R$_3$, R$_4$ and R$_5$ are all H. In particularly preferred compounds in this group, A is S(O)$_p$ or 0; p is 0; 9 is 0; n is 3; and R$_2$, R$_3$, R$_4$ and R$_5$ are all H.

In one group of preferred compounds of formula 1. A is S(O)$_p$; p is 0, 1 or 2; g is 0, 1, 2, 3, or 4; n is 2; R$_1$ is a) halo, b) an alkyl group containing 1 to 3 carbon atoms optionally substituted by one or more halo, c) an alkoxy group containing 1 to 3 carbon atoms optionally substituted by one or more halo, d) an alkylthio group, an alkylsulphinyl group or an alkylsulphonyl group each containing 1 1to 3 carbon atoms optionally substituted by one or more halo, e) hydroxy, f) an acyloxy group containing 1 to 3 carbon atoms, g) a hydroxyalkyl group containing 1 to 3 carbon atoms, h) cyano, i) an alkanoyl group containing 1 to 6 carbon atoms, j) an alkoxycarbonyl group containing 2 to 6 carbon atoms, k) a carbamoyl group or a carbamoylmethyl group each optionally N-substituted by one or two alkyl groups each containing 1 to 3 carbon atoms, l) a sulphamoyl or sulphamoylmethyl group each optionally N-substituted by one or two alkyl groups each containing 1 to 3 carbon atoms, or m) an amino group optionally substituted by one or two alkyl groups each containing 1 to 3 carbon atoms; R$_1$ being the same or different when g is 2, 3 or 4; R$_2$, R$_3$ and R$_4$ independently are H or an alkyl group containing 1 to 3 carbon atoms optionally substituted by one or more halo; and R$_5$ is H, halo, or an alkyl group containing 1 to 3 carbon atoms optionally substituted by one or more halo. Preferably, p is 0.

In more preferred compounds in this group, p is 0; g is 0 or 1; $R_1$ is halo, an alkoxy group containing 1 to 3 carbon atoms, or cyano; $R_2$, $R_3$, $R_4$ and $R_5$ are all H; and n is 2. In particularly preferred compounds in this group, p is 0; g is 0 or 1; $R_1$ is halo, an alkoxy group containing 1 to 3 carbon atoms, or cyano; $R_2$, $R_3$, $R_4$ and $R_5$ are all H; n is 2; and when g is 1, the substituent $R_1$ is in the 5-position of the benzo[b]thiophen ring system. In especially preferred compounds in this group, p is 0; n is 2; g is 0 or 1; $R_2$, $R_3$, $R_4$ and $R_5$ are all H; and when g is 1, $R_1$ is chloro, fluoro, methoxy, or cyano. Most preferably, in compounds in this group in which p is 0; n is 2; g is 0 or 1; $R_2$, $R_3$, $R_4$ and $R_5$ are all H; and when g is 1, the substituent $R_1$ is in the 5-position of the benzo[b]thiophen ring system.

In another group of preferred compounds of formula 1, A is 0; g is 0, 1, 2, 3, or 4; n is 2; $R_1$ is a) halo, b) an alkyl group containing 1 to 3 carbon atoms optionally substituted by one or more halo, c) an alkoxy group containing 1 to 3 carbon atoms optionally substituted by one or more halo, d) an alkylthio group, an alkylsulphinyl group or an alkylsulphonyl group each containing 1 to 3 carbon atoms optionally substituted by one or more halo, e) hydroxy, f) an acyloxy group containing 1 to 3 carbon atoms, g) a hydroxyalkyl group containing 1 to 3 carbon atoms, h) cyano, i) an alkanoyl group containing 1 to 6 carbon atoms, j) an alkoxycarbonyl group containing 2 to 6 carbon atoms, k) a carbamoyl group or a carbamoylmethyl group each optionally N-substituted by one or two alkyl groups each containing 1 to 3 carbon atoms, l) a sulphamoyl or sulphamoylmethyl group each optionally N-substituted by one or two alkyl groups each containing 1 to 3 carbon atoms, or m) an amino group optionally substituted by one or two alkyl groups each containing 1 to 3 carbon atoms; $R_1$ being the same or different when g is 2, 3 or 4; $R_2$, $R_3$ and $R_4$ independently are H or an alkyl group containing 1 to 3 carbon atoms optionally substituted by one or more halo; and $R_5$ is H, halo, or an alkyl group containing 1 to 3 carbon atoms optionally substituted by one or more halo.

In more preferred compounds in this group, n is 2; g is 0 or 1; $R_1$ is halo, an alkoxy group containing 1 to 3 carbon atoms, or cyano; $R_2$, $R_3$, $R_4$ and $R_5$ are all H; and n is 2. In particularly preferred compounds in this group, n is 2; g is 0 or 1; $R_1$ is halo, an alkoxy group containing 1 to 3 carbon atoms, or cyano; $R_2$, $R_3$, $R_4$ and $R_5$ are all H; n is 2; and when g is 1, the substituent $R_1$ is in the 5-position of the benzo[b]furan ring system. In especially preferred compounds in this group, n is 2; $R_2$, $R_3$, $R_4$ and $R_5$ are all H; and g is 0.

Compounds of formula I may exist as salts with pharmaceutically acceptable acids. Examples of such salts include hydrochlorides, hydrobromides, sulphates, methanesulphonates, nitrates, maleates, acetates, citrates, fumarates, tartrates [eg (+)-tartrates, (−)-tartrates or mixtures thereof including racemic mixtures], succinates, benzoates and salts with amino acids such as glutamic acid. Compounds of formula I and their salts may exist in the form of solvates (for example hydrates).

Certain compounds of formula I contain one or more chiral centres, and exist in different optically active forms. When compounds of formula I contain one chiral centre, the compounds exist in two enantiomeric forms and the present invention includes both enantiomers and mixtures of enantiomers. The enantiomers may be resolved by methods known to those skilled in the art, for example by formation of diastereoisomeric salts which may be separated, for example, by crystallisation; formation of diastereoisomeric derivatives or complexes which may be separated, for example, by crystallisation, gas-liquid or liquid chromatography; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step is required to liberate the desired enantiomeric form. Alternatively, specific enantiomers may be synthesised by asymmetric synthesis using optically active reagents, substrates, catalysts or solvents, or by converting one enantiomer into the other by asymmetric transformation.

When a compound of formula I contains more than one chiral centre it may exist in diastereoisomeric forms. The diastereoisomeric pairs may be separated by methods known to those skilled in the art, for example chromatography or crystallisation and the individual enantiomers within each pair may be separated as described above. The present invention includes each diastereoisomer of compounds of formula I and mixtures thereof.

Certain compounds of formula I may exist in different tautomeric forms or as different geometric isomers, and the present invention includes each tautomer and/or geometric isomer of compounds of formula I and mixtures thereof.

Certain compounds of formula I may exist in different stable conformational forms which may be separable. For example, if $R_4$ and/or $R_5$ are bulky groups there may be restricted rotation about one or more single bond or bonds due to steric hindrance. Torsional asymmetry due to restricted rotation about an asymmetric single bond, for example because of steric hindrance or ring strain, may permit separation of different conformers. The present invention includes each conformational isomer of compounds of formula I and mixtures thereof.

Certain compounds of formula I and their salts may exist in more than one crystal form and the present invention includes each crystal form and mixtures thereof. Certain compounds of formula I and their salts may also exist in the form of solvates, for example hydrates, and the present invention includes each solvate and mixtures thereof.

It will be understood that in compounds of formula I in which g is 0, the substituent $R_1$ is not present and all substitution positions on the benz ring are occupied by H. It will also be understood that the term Ph when used in formulae represents phenyl, and Me represents methyl.

Specific compounds of formula I are:
3-(benzo[b]thiophen-3-yl)-5,6-dihydroimidazo[2,1-b]thiazole;
3-(benzo[b]thiophen-3-yl)-6,7-dihydro-5H-thiazolo[3,2-a]pyrimidine;
3-(benzo[b]furan-3-yl)-5,6-dihydroimidazo[2,1-b]thiazole;
3-(benzo[b]furan-3-yl)-6,7-dihydro-5H-thiazolo[3,2-a]pyrimidine;
3-(5-chlorobenzo[b]thiophen-3-yl)-5,6-dihydroimidazo[2,1-b]thiazole;
3-(5-methoxybenzo[b]thiophen-3-yl)-5,6-dihydroimidazo[2,1-b]thiazole;
3-(5-fluorobenzo[b]thiophen-3-yl)-5,6-dihydroimidazo[2,1-b]thiazole;
3-(5,6-dihydroimidazo[2,1-b]thiazol-3-yl)benzo[b]thiophen-5-carbonitrile;
and pharmaceutically acceptable salts thereof.

The present invention also includes pharmaceutical compositions comprising a therapeutically effective amount of a compound of formula I or a salt thereof together with a pharmaceutically acceptable diluent or carrier.

As used hereinafter, the term "active compound" denotes a compound of formula I or a salt thereof. In therapeutic use, the active compound may be administered orally, rectally, parenterally or topically, preferably orally. Thus the therapeutic compositions of the present invention may take the form of any of the known pharmaceutical compositions for oral, rectal, parenteral or topical administration. Pharmaceutically acceptable carriers suitable for use in such compositions are well known in the art of pharmacy. The compositions of the invention may contain 0.1–99% by weight of active compound. The compositions of the invention are generally prepared in unit dosage form. Preferably the unit dosage of active ingredient is 1–500 mg. The excipients used in the preparation of these compositions are the excipients known in the pharmacist's art.

Compositions for oral administration are the preferred compositions of the invention and these are the known pharmaceutical forms for such administration, for example tablets, capsules, syrups and aqueous or oil suspensions. The excipients used in the preparation of these compositions are the excipients known in the pharmacist's art. Tablets may be prepared by mixing the active compound with an inert diluent such as calcium phosphate in the presence of disintegrating agents, for example maize starch, and lubricating agents, for example magnesium stearate, and tableting the mixture by known methods. The tablets may be formulated in a manner known to those skilled in the art so as to give a sustained release of the compounds of the present invention. Such tablets may, if desired, be provided with enteric coatings by known methods, for example by the use of cellulose acetate phthalate. Similarly, capsules, for example hard or soft gelatin capsules, containing the active compound with or without added excipients, may be prepared by conventional means and, if desired, provided with enteric coatings in a known manner. The tablets and capsules may conveniently each contain 1 to 500 mg of the active compound. Other compositions for oral administration include, for example, aqueous suspensions containing the active compound in an aqueous medium in the presence of a non-toxic suspending agent such as sodium carboxymethylcellulose, and oily suspensions containing a compound of the present invention in a suitable vegetable oil, for example arachis oil.

Solid oral dosage forms may be formulated in a manner known to those skilled in the art so as to give a sustained release of the active compound. Enteric coated, solid oral dosage forms comprising compositions of the present invention may be advantageous, depending on the nature of the active compound. Various materials, for example shellac and/or sugar, may be present as coatings, or to otherwise modify the physical form of the oral dosage form. For example tablets or pills may, if desired, be provided with enteric coatings by known methods, for example by the use of cellulose acetate phthalate and/or hydroxy propyl methylcellulose phthalate.

Capsules and/or caplets (for example hard or soft gelatin capsules) comprising the active compound (with or without added excipients such as a fatty oil), may be prepared by conventional means and, if desired, provided with enteric coatings in a known manner. The contents of the capsule and/or caplet may be formulated using known methods to give sustained release of the active compound.

Liquid oral dosage forms comprising compositions of the present invention may be an elixir, suspension and/or syrup (for example, aqueous suspensions containing the active compound in an aqueous medium in the presence of a non-toxic suspending agent [such as sodium carboxymethylcellulose] and/or oily suspensions containing the active compound in a suitable vegetable oil [such as arachis oil and/or sunflower oil]). Liquid oral dosage forms may also comprise one or more sweetening agent, flavouring agent, preservatives and/or mixtures thereof.

The active compound may be formulated into granules with or without additional excipients. The granules may be ingested directly by the patient or they may be added to a suitable liquid carrier (for example water) before ingestion. The granules may contain disintegrants (for example a pharmaceutically acceptable effervescent couple formed from an acid and a carbonate or bicarbonate salt) to facilitate dispersion in the liquid medium.

Preferably each of the above oral dosage forms may contain from about 1 mg to about 1000 mg, more preferably from about 5 mg to about 500 mg (for example 10 mg, 50 mg, 100 mg, 200 mg, or 400 mg) of the active compound.

Compositions of the invention suitable for rectal administration are the known pharmaceutical forms for such administration, for example, suppositories with hard fat, semi-synthetic glyceride, cocoa butter and/or polyethylene glycol bases.

Pharmaceutical compositions may also be administered parenterally (for example subcutaneously, intramuscularly, intradermally and/or intravenously [such as by injection and/or infusion] in the known pharmaceutical dosage forms for parenteral administration (for example sterile suspensions in aqueous and/or oily media and/or sterile solutions in suitable solvents, preferably isotonic with the blood of the intended patient). Parenteral dosage forms may be sterilised (for example by micro-filtration and/or using suitable sterilising agents [such as ethylene oxide]). Optionally one or more of the following pharmaceutically acceptable adjuvants suitable for parenteral administration may be added to parenteral dosage forms: local anaesthethetics, preservatives, buffering agents and/or mixtures thereof. Parenteral dosage forms may be stored in suitable sterile sealed containers (for example ampoules and/or vials) until use. To enhance stability during storage the parenteral dosage form may be frozen after filling the container and fluid (for example water) may be removed under reduced pressure.

Pharmaceutical compositions may be administered nasally in known pharmaceutical forms for such administration (for example sprays, aerosols, nebulised solutions and/or powders). Metered dose systems known to those skilled in the art (for example aerosols and/or inhalers) may be used.

Pharmaceutical compositions may be administered to the buccal cavity (for example sub-lingually) in known pharmaceutical forms for such administration (for example slow dissolving tablets, chewing gums, troches, lozenges, pastilles, gels, pastes, mouthwashes, rinses and/or powders).

Compositions for topical administration may comprise a matrix in which the pharmacologically active compounds of the present invention are dispersed so that the compounds are held in contact with the skin in order to administer the compounds transdermally. A suitable transdermal composition may be prepared by mixing the pharmaceutically active compound with a topical vehicle, such as a mineral oil, petrolatum and/or a wax, for example paraffin wax or beeswax, together with a potential transdermal accelerant such as dimethyl sulphoxide or propylene glycol. Alternatively the active compounds may be dispersed in a pharmaceutically acceptable cream or ointment base. The amount of active compound contained in a topical formulation should be such that a therapeutically effective amount of the compound is delivered during the period of time for which the topical formulation is intended to be on the skin.

The compounds of the present invention may also be administered by continuous infusion either from an external source, for example by intravenous infusion or from a source of the compound placed within the body. Internal sources include implanted reservoirs containing the compound to be infused which is continuously released for example by osmosis and implants which may be (a) liquid such as a suspension or solution in a pharmaceutically acceptable oil of the compound to be infused for example in the form of a very sparingly water-soluble derivative such as a dodecanoate salt or (b) solid in the form of an implanted support, for example of a synthetic resin or waxy material, for the compound to be infused. The support may be a single body containing all the compound or a series of several bodies each containing part of the compound to be delivered. The amount of active compound present in an internal source should be such that a therapeutically effective amount of the compound is delivered over a long period of time.

In some formulations it may be beneficial to use the compounds of the present invention in the form of particles of very small size, for example as obtained by fluid energy milling.

In the compositions of the present invention the active compound may, if desired, be associated with other compatible pharmacologically active ingredients.

The present invention also comprises the use of a compound of formula I as a medicament.

The pharmaceutical compositions containing a therapeutically effective amount of a compound of formula I may be used to treat depression, anxiety, psychoses (for example schizophrenia), tardive dyskinesia, obesity, drug addiction, drug abuse, cognitive disorders, Alzheimer's disease, senile dementia, cerebral ischaemia, obsessive-compulsive behaviour, panic attacks, social phobias, eating disorders and anorexia, non-insulin dependent diabetes mellitus, hyperglycaemia, or stress in human beings. Whilst the precise amount of active compound administered in such treatment will depend on a number of factors, for example the age of the patient, the severity of the condition and the past medical history and always lies within the sound discretion of the administering physician, the amount of active compound administered per day is in the range 1 to 1000 mg preferably 5 to 500 mg given in single or divided doses at one or more times during the day.

A further aspect of the present invention provides the use of a compound of formula I in the manufacture of a medicament for treating depression, anxiety, psychoses (for example schizophrenia), tardive dyskinesia, obesity, drug addiction, drug abuse, cognitive disorders, Alzheimer's disease, senile dementia, cerebral ischaemia, obsessive-compulsive behaviour, panic attacks, social phobias, eating disorders and anorexia, non-insulin dependent diabetes mellitus, hyperglycaemia, or stress in human beings.

The present invention also provides a method of treating depression, anxiety, psychoses (for example schizophrenia), tardive dyskinesia, obesity, drug addiction, drug abuse, cognitive disorders, Alzheimer's disease, senile dementia, cerebral ischaemia, obsessive-compulsive behaviour, panic attacks, social phobias, eating disorders and anorexia, non-insulin dependent diabetes mellitus, hyperglycaemia, or stress in human beings which comprises the administration of a therapeutically effective amount of a compound of formula I to a patient in need thereof.

Processes for the preparation of compounds of formula I will now be described. The processes are preferably carried out at atmospheric pressure.

Compounds of formula I may be prepared by dehydration of a compound of formula II

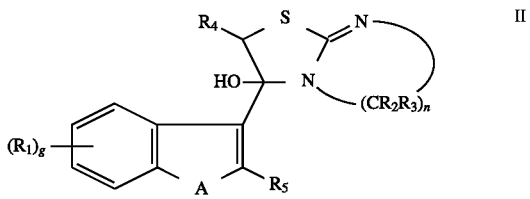

in which $A, R_1, R_2, R_3, R_4, R_5$, g and n are as hereinbefore defined, in the presence of an acid, for example acetic or sulphuric acid, at a temperature in the range 0°–200° C.; preferably in the range 20°–150° C.

Compounds of formula 11 may be prepared by reaction of a compound of formula III

III in which $R_2, R_3$ and n are as hereinbefore defined, with a compound of formula IV

IV in which Z is a leaving group, for example a halo such as bromo, and $A, R_1, R_4, R_5$ and g are as hereinbefore defined, at a temperature in the range 0°–200° C., in the presence of a solvent, for example ethanol and optionally in the presence of an acid, for example acetic acid; preferably by heating at a temperature in the range 20°–150° C.

Compounds of formula I may also be prepared directly by reaction of a compound of formula III with a compound of formula IV at a temperature in the range of 0°–200° C., optionally in the presence of an acid, for example acetic acid, and optionally in the presence of a solvent, for example ethanol, without isolation of the intermediate of formula 11; preferably by heating at a temperature in the range 20°–150° C.

Compounds of formula IV in which Z is halo may be prepared by reaction of a compound of formula V

V in which $A, R_1, R_4, R_5$ and g are as hereinbefore defined, with a halogenating agent, for example a brominating agent such as phenyltrimethylammonium tribromide or copper(II) bromide, at a temperature in the range 0°–200° C. in the presence of a solvent, for example tetrahydrofuran; preferably at a temperature in the range 20°–150° C.

Compounds of formula IV in which Z is chloro may also be prepared by reaction of a compound of formula VI

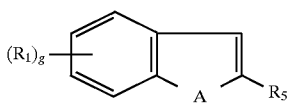

VI in which A, $R_1$, $R_5$ and g are as hereinbefore defined, with a compound of formula $R_4CH(Cl)COCl$ in the presence of a Lewis acid, for example aluminium (III) chloride or tin (IV) chloride, in a suitable solvent at a temperature in the range −20°–150° C.

Compounds of formula V may be prepared by the reaction of a compound of formula VII

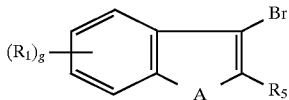

VII in which A, $R_1$, $R_5$ and g are as hereinbefore defined, with a metallating agent, for example butyllithium, followed by an acylating agent, for example a compound of formula $R_4CH_2CONMe_2$, in a suitable solvent, for example tetrahydrofuran, at a temperature in the range −60°–150° C.

Compounds of formula V may also be prepared by the reaction of a compound of formula VI with a compound of formula $R_4CH_2COCl$ in the presence of a Lewis acid, for example aluminium (Ill) chloride or tin (IV) chloride, in a suitable solvent at a temperature in the range −20°–150° C.

Compounds of formula V in which A is 0 and $R_5$ is H may be prepared by heating a compound of formula VIII

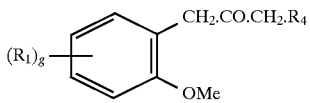

VIII in which $R_1$, $R_4$ and g are as hereinbefore defined, with dimethylformamide dimethyl acetal, at a temperature in the range 0°–150° C., followed by cooling and reaction with boron tribromide.

Compounds of formula V in which A is S and $R_4$ and $R_5$ are H may be prepared by methods described in K. C. Majumdar and B. S. Thyagarajan, International Journal of Sulphur Chemistry, A, 1972, 2, 67 and 93, as outlined below:

Compounds of formula V in which A is S, $R_4$ and $R_5$ are H, and $R_1$ and g are as hereinbefore defined may be prepared by reaction of a compound of formula IX

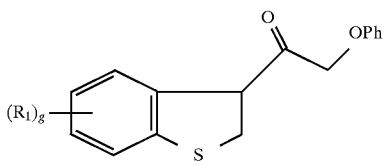

IX in which g is 0,1,2,3 or 4, with concentrated sulphuric acid, at a temperature in the range 50°–100° C. in a solvent, for example acetic acid; preferably at a temperature in the range 90°–95° C.

Compounds of formula IX may be prepared by the reaction of a compound of formula X

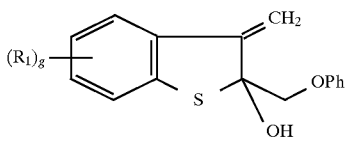

X in which $R_1$ and g are as hereinbefore defined, with a base, for example sodium hydroxide, in a solvent, for example dichloromethane, at a temperature in the range 20°–150° C.

Compounds of formula X may be prepared by heating a compound of formula XI

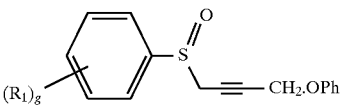

XI in which $R_1$ and g are as hereinbefore defined, in the presence of a suitable solvent, for example chloroform, at a temperature in the range 20°–150° C., preferably in the range 80°–90° C.

Compounds of formula XI may be prepared by the reaction of a compound of formula XII

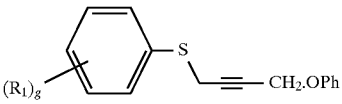

XII in which $R_1$ and g are as hereinbefore defined, with an oxidising agent, for example m-chloroperoxybenzoic acid, in a solvent, for example chloroform, at a temperature in the range 0°–40° C.

Compounds of formula XII may be prepared by the reaction of a compound of formula XIII

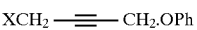

XIII in which X is a leaving group, for example a halo such as chloro, with a compound of formula XIV

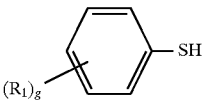

XIV in which R, and g are as hereinbefore defined, in the presence of a base, for example potassium hydroxide, in a solvent, for example a mixture of ethanol and water, at a temperature in the range 20°–150° C.

Compounds of formula XII may be prepared by the reaction of 1,4-dichlorobut-2-yne with phenol in the presence of a base, for example potassium hydroxide, in a solvent, for example a mixture of ethanol and water, at a temperature in the range 20°–150° C.

The ability of compounds of formula I to interact with 5-hydroxytryptamine (5-HT) receptors has been demonstrated by the following test which determines the ability of the compounds to inhibit tritiated ligand binding to 5-HT receptors in vitro and in particular to $5-HT_{1A}$ receptors.

Hippocampal tissue from the brains of male Sprague-Dawley rats (Charles River; weight range 150–250 g) was homogenised in ice-cold 50 mM Tris-HCl buffer (pH 7.7 when measured at 25° C., 1:40 w/v) and centrifuged at 30,000 g at 4° C. for 10 minutes. The pellet was rehomogenised in the same buffer, incubated at 37° C. for 10 minutes and centrifuged at 30,000 g at 4° C. for 10 minutes. The final pellet was resuspended in 50 mM Tris-HCl buffer (pH 7.7) containing 4 mM $CaCl_2$, 0.1% L-ascorbic acid and 10 µM pargyline hydrochloride (equivalent to 6.25 mg wet weight of tissue/ml) and used immediately in the binding assay.

Aliquots (400 µl; equivalent to 2.5 mg wet weight of tissue/tube) of this membrane preparation were added to tubes containing [$^3$H]8-hydroxy-2-(dipropylamino)tetralin ([$^3$H]8-OH-DPAT; 50 µl; 2 nM) and distilled water (50 µl; total binding) or 5-HT (50 µl; 10 µM; non-specific binding) or test compound (50 µl; at a single concentration of $10^{-6}$M or at 10 concentrations ranging from $10^{-11}$–$10^{-3}$M) and incubated at 25° C. for 30 minutes. The incubation was terminated by rapid filtration under vacuum through Skatron 11734 filters using a Skatron Cell Harvester. Filters were washed with ice-cold 50 mM Tris-HCl buffer, pH 7.7 (at 25° C., wash setting 9,9,0) and dried. The scored filter paper discs were punched out into vials, scintillation fluid added and radioactivity determined by liquid scintillation counting.

The percentage displacement of specific binding of the tritiated ligand was calculated for the single concentration ($10^{-6}$M) of test compound. Displacement curves were then produced for those compounds which displaced $\geq 50\%$ of specific binding of the tritiated ligand at $10^{-6}$M using a range of concentrations of the compound. The concentration which gave 50% inhibition of specific binding ($IC_{50}$) was obtained from the curve. The inhibition coefficient Ki was then calculated using the formula $$Ki = \frac{IC_{50}}{1 + ([\text{ligand}]/K_D)}$$

in which [ligand] is the concentration of the tritiated ligand used and $K_D$ is the equilibrium dissociation constant for the ligand.

The ability of compounds of formula I to interact with 5-hydroxytryptamine (5-HT) reuptake sites has been demonstrated by the following test which determines the ability of compounds to inhibit 5-HT uptake in vitro.

Frontal cortical tissue from the brains of male Sprague-Dawley rats (Charles River; weight range 150–250 g) was homogenised in ice-cold 0.32M sucrose (1:10 w/v) using a motor driven teflon pestle (difference in diameter between mortar and pestle 0.5 mm). Nuclei and cell debris were removed by centrifugation at 1,500 g at 4° C. for 10 minutes. The pellet (P1) was discarded and the supernatant centrifuged at 30,000 g at 4° C. for 10 minutes. The crude synaptosomal pellet (P2) was resuspended in Krebs-Henseleit buffer (equivalent to 8.3 mg wet weight of tissue/ml).

Crude synaptosomes were incubated in a shaking water bath at 37° C. for 15 minutes. Aliquots (150 µl; equivalent to 1.25 mg wet weight of tissue/tube) were then added to tubes containing 275 µl of Krebs-Henseleit buffer and 50 µl of Krebs-Henseleit buffer (total uptake) or 50 µl of test compound (at a single concentration of $10^{-6}$M or at 10 concentrations ranging from $10^{-11}$–$10^{-3}$M) or 50 µl of zimeldine ($10^{-5}$M; non-specific uptake). Uptake was initiated by the addition of 25 µl of freshly prepared [$^3$H]5-HT (2 nM), followed by vortexing, and was continued for 5 minutes at 37° C. in the shaking water bath. Uptake was terminated by filtration under vacuum through Skatron 11734 filters using a Skatron cell harvester. Filters were then washed with 8 ml ice-cold saline. The scored filter paper discs were punched into vials, scintillation fluid added and radioactivity determined by liquid scintillation counting.

The ability of compounds of formula I to interact with noradrenaline reuptake sites has been demonstrated by the following test which determines the ability of compounds to inhibit noradrenaline uptake in vitro.

Frontal cortical tissue from the brains of male Sprague-Dawley rats (Charles River; weight range 150–250 g) was homogenised in ice-cold 0.32M sucrose (1:10 w/v) using a motor driven teflon pestle (difference in diameter between mortar and pestle 0.5 mm). Nuclei and cell debris were removed by centrifugation at 1,500 g at 4° C. for 10 minutes. The pellet (P1) was discarded and the supernatant centrifuged at 30,000 g at 4° C. for 10 minutes. The crude synaptosomal pellet (P2) was resuspended in Krebs-Physiological buffer (equivalent to 16.7 mg wet weight of tissue/ml).

Crude synaptosomes were incubated in a shaking water bath at 37° C. for 15 minutes. Aliquots (150 µl; equivalent to 2.5 mg wet weight of tissue/tube) were then added to tubes containing 275 µl of Krebs-Physiological buffer and 50 µl of Krebs-Physiological buffer (total uptake) or 50 µl of test compound (at a single concentration of $10^{-6}$M or 10 concentrations ranging from $10^{-11}$–$10^{-3}$M) or 50 µl of desipramine ($10^{-5}$M; non-specific uptake). Uptake was initiated by the addition of 25 µl of freshly prepared [$^3$H] noradrenaline (10 nM), followed by vortexing and was continued for 5 minutes at 37° C. in the shaking water bath. Uptake was terminated by filtration under vacuum through Whatman GF/B filters using a Brandell cell harvester. Filters were then washed with 8 ml ice-cold saline. The scored filter paper discs were placed into vials, scintillation fluid added and radioactivity determined by liquid scintillation counting.

For both the 5-HT uptake and noradrenaline uptake tests, the percentage inhibition of specific uptake of the tritiated ligand was calculated for the single concentration ($10^{-6}$M) of test compound. Inhibition curves were then produced for those compounds which inhibited $\geq 50\%$ of specific uptake of the tritiated ligand at $10^{-6}$M using a range of concentrations of test compound. The concentration which gave 50% inhibition of specific uptake ($IC_{50}$) was obtained from the curve. The inhibition constant (Ki) was then calculated using the formula $$Ki = \frac{IC_{50}}{1 + ([\text{ligand}]/Km)}$$

in which [ligand] is the concentration of tritiated ligand used and Km is the affinity of the uptake site for the ligand.

The $K_i$ values (nM) obtained in the above tests for 5-$HT_{1A}$ binding and 5-HT and NA uptake for each of the final products of Examples 1 to 8 hereinafter are given in Table I below. Values are means of three independent determinations unless otherwise indicated. % Figures are for % displacement at $10^{-6}$M.

TABLE 1

| Example No. | 5-$HT_{1A}$ | 5-HT uptake | NA uptake |
| --- | --- | --- | --- |
| 1 | 81 | 12.7 | 2.8 |
| 2 | 340 | 305 | 40 |
| 3 | 118 | 84 | 41 |
| 4 | 321 | 881* | 116** |
| 5 | 40.7 | 8.7 | 13 |
| 6 | 37.5 | 22 | 51 |
| 7 | 66%* | 36 | 5.4 |
| 8 | 467 | 530 | NT |

*value is the mean of two independent determinations
**value is the result of one determination.
NT not tested These types of activity are indicative of a compound having utility in the treatment of central nervous system disorders, particularly depression and anxiety. Compounds of formula I may have an improved pharmacological profile over compounds known in the art.

The invention is illustrated by the following Examples which are given by way of example only. The final product of each of these Examples was characterised by one or more of the following procedures: high performance liquid chromatography; elemental analysis, nuclear magnetic resonance spectroscopy and infrared spectroscopy.

EXAMPLE 1

A solution of phenyltrimethylammonium tribromide (9.6 g) in tetrahydrofuran (20 ml) was added dropwise over 15 minutes at ambient temperature to a stirred solution of 3-acetylbenzo[b]thiophen (5 g) in tetrahydrofuran (50 ml), then the mixture was stirred at ambient temperature for 35 minutes. Water (100 ml) was added, and the resulting solid was collected by filtration, washed with water (2×50 ml) and dried in vacuo at ambient temperature to give 3-(2-bromoacetyl)benzo[b]thiophen as a white solid (2.4 g).

A mixture of 3-(2-bromoacetyl)benzo[b]thiophen (2.39 g), 2-imidazolidinethione (0.78 g), ethanol (60 ml) and acetic acid (40 ml) was heated under reflux for 18 hours then allowed to cool to ambient temperature. The resulting solid was collected by filtration, washed with ether (2×50 ml), and dried in vacuo at ambient temperature to give 3-(benzo[b]thiophen-3-yl)-5,6-dihydroimidazo[2,1-b]thiazole monohydrobromide dihydrate as a white solid (2.96 g), m.p. 239°–240° C.

Alternative Preparation

Phenyltrimethylammonium tribromide (26.32 g) was added in portions over 45 minutes at −5° C. under nitrogen to a stirred solution of 3-acetylbenzo[b]thiophen (12.34 g) in tetrahydrofuran (100 ml), then the mixture was stirred at ambient temperature for 1 hour. The resulting solid was collected by filtration, washed with ether (100 ml), dried in vacuo at ambient temperature, and crystallised from ethanol to give 3-(2-bromoacetyl)benzo[b]thiophen as a white solid (10.9 g).

A mixture of 3-(2-bromoacetyl)benzo[b]thiophen (10.0 g), 2-imidazolidinethione (4.0 g), ethanol (120 ml) and acetic acid (80 ml) was heated under reflux for 24 hours then allowed to cool to ambient temperature. The resulting solid was collected by filtration and dried in vacuo at ambient temperature to give 3-(benzo[b]thiophen-3-yl)-5,6-dihydroimidazo[2,1-b]thiazole monohydrobromide 1.8 hydrate as a white solid (11.6 g), m.p. 227°–229° C.

EXAMPLE 2

A mixture of 3-(2-bromoacetyl)benzo[b]thiophen (3.35 g; prepared in a similar manner to that described in Example 1, Alternative Preparation), 3,4,5,6-tetrahydro-2-pyrimidinethiol (1.5 g), ethanol (150 ml) and acetic acid (100 ml) was heated under reflux for 18 hours, then the solvents were removed in vacuo to leave a hygroscopic orange solid (4.96 g). A mixture of the orange solid (4.84 g) and 5M sulphuric acid (50 ml) was heated at 90°–95° C. for 18 hours then allowed to cool to ambient temperature. The resulting solid was collected by filtration, washed with ether (3×50 ml) and dried in vacuo at ambient temperature to give 3-(benzo[b]thiophen-3-yl)-6,7-dihydro-5H-thiazolo[3,2-a]pyrimidine 0.1 hydrobromide 0.45 sulphate as a pale pink solid (4.92 g). The mixture of salts (3 g) was basified by the addition of an excess of 1M aqueous sodium hydroxide solution, and the product was extracted into dichloromethane (3×45 ml). The extracts were dried (MgSO$_4$), and the solvent removed in vacuo to leave 3-(benzo[b]thiophen-3-yl)-6,7-dihydro-5H-thiazolo[3,2-2a]pyrimidine as a cream solid (1.73 g), m.p. 155°–158° C.

EXAMPLE 3

A mixture of 1-(2-methoxyphenyl)propan-2-one (10 g) and dimethylformamide dimethyl acetal (17.8 g) was stirred at 80° C, under nitrogen for 4 hours, then concentrated in vacuo to leave a viscous oil. The oil was disolved in dichloromethane (80 ml), and the solution was stirred and cooled in an ice-bath while boron tribromide (1M solution in dichloromethane; 104 ml) was added dropwise over 15 minutes. When the addition was complete, the mixture was stirred, with ice-cooling, for a further 1.5 hours, then it was poured into an excess of ice and saturated aqueous sodium hydrogen carbonate solution. The product was extracted into dichloromethane (3×200 ml) and the combined extracts were washed with water (2×200 ml), dried (Na$_2$SO$_4$), and the solvent removed in vacuo to leave 3-acetylbenzo[b]furan as a dark red oil (4.25 g).

A solution of phenyltrimethylammonium tribromide (2.47 g) in tetrahydrofuran (20 ml) was added dropwise at ambient temperature under nitrogen over 5 minutes to a stirred solution of 3-acetylbenzo[b]furan (1 g) in tetrahydrofuran (20 ml), then the mixture was stirred at ambient temperature for a further 1.5 hours, filtered, and the solvent removed in vacuo. The residue was triturated with ether, and the resulting solid was collected by filtration and dried in vacuo at ambient temperature to give 3-(2-bromoacetyl)benzo[b]furan as an off-white solid (0.25 g).

A mixture of 3-(2-bromoacetyl)benzo[b]furan (0.25 g), 2-imidazolidinethione (0.11 g), ethanol (30 ml) and acetic acid (20 ml) was heated under reflux for 20 hours, then allowed to cool to ambient temperature. The resulting solid was collected by filtration, washed with ether, and dried in vacuo at ambient temperature to give 3-(benzo[b]furan-3-yl)-5,6-dihydroimidazo[2,1-b]thiazole monohydrobromide monohydrate as a white solid (0.145 g), m.p. 242°–244° C.

Alternative Preparation

A mixture of 1-(2-methoxyphenyl)propan-2-one (77.2 g) and dimethylformamide dimethyl acetal (137.5 g) was stirred at 80° C. under nitrogen for 4 hours, then concentrated in vacuo to leave a viscous oil. The oil was dissolved in dichloromethane (620 ml) then the stirred solution was cooled to 0° C. Boron tribromide (1M solution in dichloromethane, 800 ml) was added dropwise over 1.75 hours at 0°–5° C., then the mixture was stirred at 0°–5° C. for a further 1.5 hours and poured onto an excess of ice and saturated aqueous sodium hydrogen carbonate solution. Solid sodium hydrogen carbonate was added in portions with occasional stirring until effervescence ceased. The product was extracted into dichloromethane (3×600 ml) then the combined extracts were washed with water (2×600 ml), dried (Na$_2$SO$_4$), and the solvent removed in vacuo to leave 3-acetylbenzo[b]furan as a brown oil (78.9 g).

A stirred suspension of freshly-ground copper(II) bromide (87.4 g) in ethyl acetate (625 ml) was heated to reflux temperature under nitrogen, then a solution of 3-acetylbenzo[b]furan (40 g) in chloroform (625 ml) was added. The mixture was then heated under reflux, with vigorous stirring, for 5 hours, allowed to stand at ambient temperature for 48 hours, heated under reflux for 1 hour, cooled to ambient temperature, and filtered. The solvents were removed in vacuo, the residue was triturated with ether (1l), and the resulting solid was collected by filtration, ground to a fine powder, and dried in vacuo at ambient temperature to give 3-( 2-bromoacetyl)benzo[b]furan as a dark grey solid (26 g). Concentration of the ethereal liquor yielded a second crop of grey solid (10.9 g).

A mixture of 3-(2-bromoacetyl)benzo[b]furan (36.9 g), 2-imidazolidinethione (15.75 g), ethanol (600 ml) and acetic acid (400 ml) was heated under reflux for 21 hours then allowed to cool to ambient temperature. The resulting solid was collected by filtration, washed with ether (500 ml), and dissolved in hot methanol (500 ml). Charcoal (2 g) was added and the hot mixture was stirred for a few minutes, then filtered and allowed to cool to ambient temperature. The resulting solid was collected by filtration, ground to a fine powder, and dried in vacuo at 80° C. to give 3-(benzo[b]

furan-3-yl)-5,6-dihydroimidazo[2,1-b]thiazole monohydrobromide 0.7 hydrate as an off-white solid (28.1 g), m.p. 251°–254.50C.

EXAMPLE 4

A stirred suspension of copper(II) bromide (3.95 g) in a mixture of chloroform (25 ml) and ethyl acetate (25 ml) was heated to reflux temperature, and 3-acetyl-benzo[b]furan (1.7 g; prepared as described in Example 3, Alternative Preparation) was added. The stirred mixture was heated under reflux for 1 hour, cooled to ambient temperature, filtered, and the solvents removed in vacuo. The residue was dissolved in a mixture of ethanol (30 ml) and acetic acid (20 ml), 3,4,5,6-tetrahydro-2-pyrimidinethiol (0.25 g) was added, and the mixture was heated under reflux for 18 hours. The solvents were removed in vacuo, 1M sulphuric acid (20 ml) was added, then the mixture was heated at 90°–95° C. for 48 hours, cooled to ambient temperature, and basified by the addition of 1M aqueous sodium hydroxide solution. The product was extracted into chloroform (3×20 ml), then the combined extracts were dried ($Na_2SO_4$) and the solvent removed in vacuo to give 3-(benzo[b]furan-3-yl)-6,7-dihydro-5H-thiazolo[3,2-a]pyrimidine as a pale yellow solid (0.15 g), m.p. 128°–130° C.

EXAMPLE 5

A mixture of phenol (50.8 g), potassium hydroxide (30 g), ethanol (200 ml) and water (50 ml) was stirred and heated under reflux for 1 hour, then cooled to 30° C. A solution of 1,4-dichlorobut-2-yne (100 g) in ethanol (60 ml) was added dropwise over 3.5 hours, then the mixture was stirred at ambient temperature for 18 hours and filtered. The filter cake was washed with ethanol (60 ml), and the filtrate and washings were combined. The solvents were removed in vacuo, and the residue was distilled to give 1-chloro-4-phenoxybut-2-yne as a colourless oil (52.5 g), b.p. 92°–98° C. at 0.53 mbar.

A solution of potassium hydroxide (16.3 g) in a mixture of ethanol (480 ml) and water (120 ml) was added at ambient temperature under nitrogen to a stirred solution of 4-chlorothiophenol (42 g) in a mixture of ethanol (425 ml) and water (25 ml), then the mixture was stirred at ambient temperature for 4 hours. A solution of 1-chloro-4-phenoxybut-2-yne (52.5 g) in a mixture of ethanol (425 ml) and water (25 ml) was added dropwise over 3 hours, then the mixture was stirred at ambient temperature for 18 hours, and filtered. The filter cake was washed with water (500 ml), then the combined filtrate and washings were concentrated in vacuo to remove the ethanol. The product was extracted from the aqueous residue using ethyl acetate (2×250 ml), then the combined extracts were washed with water (100 ml) and saturated brine (50 ml), dried ($MgSO_4$), and the solvent removed in vacuo to leave a 4:1 mixture of 1-(4-chlorophenylthio)-4-phenoxybut-2-yne and 1-chloro-4-phenoxybut-2-yne as a pale yellow oil (79.65 g) which was used without purification.

A solution of m-chloroperoxybenzoic acid (55% purity; 81 g) in dichloromethane (1400 ml) was added dropwise over 2.5 hours to a stirred, ice-cold solution of the crude 1-(4-chlorophenylthio)-4-phenoxybut-2-yne (74.5 g) in dichloromethane (600 ml), then the mixture was stirred at ambient temperature for 18 hours and filtered. The filtrate was washed with 5% aqueous sodium carbonate solution (3×750 ml) and water (3×500 ml) then dried ($Na_2SO_4$), and the solvent removed in vacuo. The residue was dissolved in hot dichloromethane (40 ml), then petroleum ether (b.p. 60°–80° C.) (75 ml) was added, and the mixture was triturated to give a sticky solid which was collected by filtration, triturated with hot ether (500 ml), collected by filtration, and dried in vacuo to give 1-(4-chlorophenylsulphinyl)-4-phenoxybut-2-yne as a solid (21.73 g), m.p. 102°–103° C.

A mixture of 1-(4-chlorophenylsulphinyl)-4-phenoxybut-2-yne (17.45 g) and chloroform (150 ml) was heated under nitrogen at an external temperature of 80°–85° C. for 5 hours, and the solvent was removed in vacuo to leave 5-chloro-3-methylene- 2-phenoxymethyl-2,3-dihydrobenzo[b]thiophen-2-ol as a viscous yellow-green oil (17.45 g).

A solution of 5-chloro-3-methylene-2-phenoxymethyl-2, 3-dihydrobenzo[b]-thiophen-2-ol (16.9 g) in dichloromethane (250 ml) was shaken vigorously for a few seconds with 5M aqueous sodium hydroxide solution (150 ml), then the organic solution was separated, washed with water (150 ml), dried ($MgSO_4$), and the solvent removed in vacuo to leave 1-(5-chloro-2,3-dihydrobenzo[b]thiophen-3-yl)-2-phenoxyethanone as a pink solid (16.4 g) which was used without further purification.

A mixture of 1-(5-chloro-2,3-dihydrobenzo[b]thiophen-3-yl)-2-phenoxyethanone (15.3 g), acetic acid (75 ml) and concentrated sulphuric acid (15 drops) was heated at 90°–95° C. under nitrogen for 20 hours, then the solvent was removed in vacuo. The residue was partitioned between dichloromethane (250 ml) and 5M aqueous sodium hydroxide solution (100 ml), then the aqueous phase was separated and washed with dichloromethane (50 ml). The combined dichloromethane solutions were washed with water (100 ml), dried ($MgSO_4$), and the solvent removed in vacuo to leave 3-acetyl-5-chlorobenzo[b]thiophen as a red-brown oil (10.7 g) which solidified slowly at ambient temperature.

Phenyltrimethylammonium tribromide (3.6 g) was added in portions under nitrogen over 30 minutes to a stirred suspension of 3-acetyl-5-chlorobenzo[b]thiophen (2 g) in tetrahydrofuran (25 ml), then the mixture was stirred at ambient temperature for 3 hours and filtered. The filter cake was washed with tetrahydrofuran (10 ml), then the filtrate and washings were combined, and the solvent removed in vacuo to leave 3-(2-bromoacetyl)-5-chlorobenzo[b]thiophen as a grey solid (4.2 g) which was used without purification.

A mixture of the crude 3-(2-bromoacetyl)-5-chlorobenzo[b]thiophen (4.2 g), 2-imidazolidinethione (1 g), ethanol (15 ml) and acetic acid (10 ml) was heated under reflux under nitrogen for 18 hours, then allowed to cool to ambient temperature. The resulting solid was collected by filtration, washed with ethanol (15 ml), and dried in vacuo to give 3-(5-chlorobenzo[b]thiophen-3-yl)-5,6-dihydroimidazo[2, 1-b]thiazole monohydrobromide as a white solid (2.1 g), m.p. 286°–288° C. (dec.).

EXAMPLE 6

A solution of potassium hydroxide (14.9 g) in a mixture of ethanol (450 ml) and water (110 ml) was added at ambient temperature under nitrogen to a stirred solution of 4-methoxythiophenol (32.7 g) in a mixture of ethanol (400 ml) and water (25 ml), then the mixture was stirred at ambient temperature for 4 hours. A solution of 1-chloro-4-phenoxybut-2-yne (48 g; prepared in a similar manner to that described in Example 5) in a mixture of ethanol (400 ml) and water (25 ml) was added dropwise over 3 hours, then the mixture was stirred at ambient temperature for 18 hours. The mixture was concentrated in vacuo to remove the ethanol, then the product was extracted into ethyl acetate (2×250 ml). The combined extracts were washed with water (100 ml) and saturated brine (50 ml), dried (MgSO$_4$), and the solvent removed in vacuo to leave a 9:1 mixture of 1-(4-methoxyphenylthio)-4-phenoxybut-2-yne and 1,4-bis-(4-methoxyphenylthio)but-2-yne as an oil (76.9 g) which was used without purification.

A solution of m-chloroperoxybenzoic acid (55% purity; 84.9 g) in dichloromethane (1400 ml) was added dropwise over 2.5 hours to a stirred, ice-cold solution of the crude 1-(4-methoxyphenylthio)-4-phenoxybut-2-yne (76.9 g) in dichloromethane (600 ml), then the mixture was stirred at ambient temperature for 18 hours and filtered. The filtrate was washed with 5% aqueous sodium carbonate solution (3×750 ml) and water (3×500 ml), then dried (Na$_2$SO$_4$) and divided into two equal portions.

The solvent was removed from the first portion by distillation at atmospheric pressure, to leave crude 1-(4-methoxyphenylsulphinyl)-4-phenoxybut-2-yne as a dark brown gum (44 g).

The solvent was removed in vacuo from the second portion to leave crude 1-(4-methoxyphenylsulphinyl)-4-phenoxybut-2-yne as an orange-yellow gum (31.4 g).

NMR analysis of both gums indicated the second to be of higher purity, so this was used in the subsequent stages. A mixture of the crude 1-(4-methoxyphenylsulphinyl)-4-phenoxybut-2-yne (2.1 g) and chloroform (25 ml) was heated under nitrogen at an external temperature of 80°–85° C. for 1 hour, allowed to stand at ambient temperature for 18 hours, and heated at an external temperature of 90°–95° C. for 6 hours. The solvent was removed by distillation to leave crude 5-methoxy-3-methylene-2-phenoxymethyl-2,3-dihydrobenzo[b]thiophen-2-ol as an orange gum. The orange gum was dissolved in dichloromethane (30 ml) and the solution was shaken vigorously for a few seconds with 5M aqueous sodium hydroxide solution (25 ml), then the organic solution was separated, washed with water (25 ml), dried (MgSO$_4$), and the solvent removed in vacuo to leave crude 1-(5-methoxy-2,3-dihydrobenzo[b]thiophen-3-yl)-2-phenoxyethanone as a red gum (1.94 g) which was used without purification.

A mixture of the crude 1-(5-methoxy-2,3-dihydrobenzo[b]thiophen-3-yl)-2-phenoxyethanone (1.94 g), acetic acid (10 ml) and concentrated sulphuric acid (2 drops) was heated at 90°–95° C. for 18 hours, then the solvent was removed in vacuo. The residue was partitioned between dichloromethane (50 ml) and 5M aqueous sodium hydroxide solution (30 ml), then the aqueous phase was separated and washed with dichloromethane (30 ml). The combined dichloromethane solutions were washed with water (30 ml), dried (MgSO$_4$), and the solvent removed in vacuo to leave a brown gum (1.3 g). The gum was purified by flash chromatography over silica using 10–15% mixtures of ethyl acetate and petroleum ether (b.p. 60°–80° C.) as eluants. Appropriate fractions were combined, and the solvents removed in vacuo to leave 3-acetyl-5-methoxybenzo[b]thiophen as a pale brown gum (0.37 g).

Phenytrimethylammonium tribromide (0.66 g) was added in portions under nitrogen over 30 minutes to a stirred solution of 3-acetyl-5-methoxybenzo[b]thiophen (0.36 g) in tetrahydrofuran (5 ml), then the mixture was stirred at ambient temperature for 1.75 hours and filtered. The filter cake was washed with tetrahydrofuran (5 ml), then the filtrate and washings were combined, and the solvent was removed in vacuo. The residue was dissolved in ethanol (8 ml), acetic acid (2 ml) and 2-imidazolidinethione (0.18 g) were added, and the mixture was heated under reflux under nitrogen for 18 hours, then allowed to cool to ambient temperature. The resulting solid was collected by filtration, washed with ethanol (5 ml), and dried in vacuo at 70° C. to give 3-(5-methoxybenzo[b]thiophen-3-yl)-5,6-dihydroimidazo[2,1-b]thiazole monohydrobromide as a beige solid (0.3 g), m.p. 246°–248° C.

Alternative Preparation

A solution of potassium hydroxide (3.4 g) in a mixture of ethanol (110 ml) and water (28 ml) was added dropwise at ambient temperature under nitrogen to a stirred solution of 4-methoxythiophenol (8.55 g) in a mixture of ethanol (100 ml) and water (6.5 ml), then the mixture was stirred at ambient temperature for 3.5 hours. A solution of 1-chloro-4-phenoxybut-2-yne (11 g; prepared in a similar manner to that described in Example 5) in a mixture of ethanol (100 ml) and water (6.5 ml) was added dropwise over 1.5 hours, then the mixture was stirred at ambient temperature for 18 hours. The mixture was concentrated in vacuo to remove the ethanol, then the product was extracted into ethyl acetate (2×80 ml). The combined extracts were washed with water (30 ml) and saturated brine (20 ml), dried (MgSO$_4$), and the solvent removed in vacuo to leave an oil (17.7 g). The oil was purified by flash chromatography over silica using 10–20% mixtures of ethyl acetate and petroleum ether (b.p. 60°–80° C.) as eluants. Appropriate fractions were combined and the solvents removed in vacuo to leave 1-(4-methoxyphenylthio)-4-phenoxybut-2-yne as an oil (13.7 g).

A solution of m-chloroperoxybenzoic acid (55% purity; 15.2 g) in chloroform (300 ml) was added dropwise over 2.5 hours to a stirred, ice-cold solution of 1-(4-methoxyphenylthio)-4-phenoxybut-2-yne(13.7 g) in chloroform (125 ml), then the mixture was stirred at ambient temperature for 18 hours and filtered. The filtrate was washed with 5% sodium carbonate solution (3×150 ml) and water (3×100 ml), then dried (MgSO$_4$) and filtered. The filtrate was heated under nitrogen at an external temperature of 80°–85° C. for 6 hours, allowed to stand at ambient temperature for 18 hours, heated at an external temperature of 80°–85° C. for a further 1.5 hours, then allowed to cool. The solvent was removed in vacuo, the residue was dissolved in dichloromethane (250 ml), and the solution was shaken vigorously for a few seconds with 5M aqueous sodium hydroxide solution (150 ml). The organic solution was separated, washed with water (2×150 ml), dried (MgSO$_4$), and the solvent removed in vacuo. The residue was purified by flash chromatography over silica using 12.5–25% mixtures of ethyl acetate and petroleum ether (b.p. 60°–80° C.) as eluants. Appropriate fractions were combined, and the solvents removed in vacuo to leave 1-(5-methoxy-2,3-dihydrobenzo[b]thiophen-3-yl)-2-phenoxyethanone as a gum (4.5 g).

A mixture of 1-(5-methoxy-2,3-dihydrobenzo[b]thiophen-3-yl)-2-phenoxyethanone (4.5 g), acetic acid (20 ml) and concentrated sulphuric acid (5 drops) was heated under nitrogen at 90°–95° C. for 3 hours, then the solvent was removed in vacuo. The residue was partitioned between dichloromethane (100 ml) and 5M aqueous sodium hydroxide solution (50 ml), then the aqueous phase was separated and washed with dichloromethane (50 ml). The combined dichloromethane solutions were washed with water (50 ml), dried (MgSO$_4$), and the solvent removed in vacuo to leave an orange-brown oil (3.2 g). The oil was purified by flash chromatography over silica using 20–25% mixtures of ethyl acetate and petroleum ether (b.p. 60°–80° C.) as eluants. Appropriate fractions were combined and the solvents removed in vacuo to leave 3-acetyl-5-methoxybenzo[b]thiophen as an off-white solid (1.8 g).

Phenyltrimethylammonium tribromide (3.3 g) was added in portions under nitrogen over 30 minutes to a stirred solution of 3-acetyl-5-methoxybenzo[b]thiophen (1.8 g) in tetrahydrofuran (20 ml), then the mixture was stirred at ambient temperature for 1 hour and filtered. The filter cake was washed with tetrahydrofuran (20 ml), then the filtrate and washings were combined and the solvent removed in vacuo. The residue was dissolved in ethanol (25 ml), acetic acid (18 ml) and 2-imidazolidinethione (0.9 g) were added, and the mixture was heated under reflux under nitrogen for 18 hours, then allowed to cool to ambient temperature. The resulting solid was collected by filtration, washed with ethanol (25 ml), and dried in vacuo at 70° C. to give 3-(5-methoxybenzo[b]thiophen-3-yl)-5,6-dihydroimidazo[2,1-b]thiazole monohydrobromide as a white solid (1.55 g), m.p. 246°–248° C.

EXAMPLE 7

A solution of potassium hydroxide (11.5 g) in a mixture of ethanol (340 ml) and water (85 ml) was added at ambient temperature under nitrogen to a stirred solution of 4-fluorothiophenol (26.3 g) in a mixture of ethanol (300 ml) and water (18 ml), then the mixture was stirred at ambient temperature for 4 hours. A solution of 1-chloro-4-phenoxybut-2-yne (37 g; prepared in a similar manner to that described in Example 5) in a mixture of ethanol (300 ml) and water (18 ml) was added dropwise over 1.5 hours, then the mixture was stirred at ambient temperature for 24 hours. The mixture was concentrated in vacuo to remove the ethanol, then the product was diluted with water (100 ml) and extracted into ethyl acetate (2× 250 ml). The combined extracts were washed with water (100 ml) and saturated brine (100 ml), dried (MgSO$_4$), and the solvent removed in vacuo to leave a yellow oil (59.2 g). The oil partially solidified at ambient temperature, and the solid was collected by filtration, washed with petroleum ether (b.p. 40°–60° C.) and dried in vacuo at ambient temperature to give 1-(4-fluorophenylthio)-4-phenoxybut-2-yne as a white solid (39.3 g).

A solution of m-chloroperoxybenzoic acid (55% purity; 23.1 g) in chloroform (450 ml) was added dropwise over 2.75 hours to a stirred, ice-cold solution of 1-(4-fluorophenylthio)-4-phenoxybut-2-yne (20 g) in chloroform (190 ml), then the mixture was stirred at ambient temperature for 18 hours and filtered. The filtrate was washed with 5% aqueous sodium carbonate solution (3×230 ml) and water (3×150 ml), then dried (MgSO$_4$), and refiltered.

The filtrate was heated under nitrogen at an external temperature of 80°–85° C. for 1.5 hours, allowed to stand at ambient temperature for 18 hours, heated at an external temperature of 80°–85° C. for 7 hours, and allowed to stand at ambient temperature for 65 hours. The solvent was removed in vacuo to leave crude 5-fluoro-3-methylene-2-phenoxymethyl-2,3-dihydrobenzo[b]thiophen-2-ol as a viscous yellow oil (22.45 g).

The oil was dissolved in dichloromethane (380 ml) and the solution was shaken vigorously for a few seconds with 5M aqueous sodium hydroxide solution (230 ml), then the organic solution was separated, washed with water (4×230 ml), and dried (MgSO$_4$). The solvent was removed in vacuo to leave crude 1-(5-fluoro-2,3-dihydrobenzo[b]thiophen-3-yl)-2-phenoxyethanone as a pink oil (20.6 g) which solidified slowly at ambient temperature.

A mixture of the crude 1-(5-fluoro-2,3-dihydrobenzo[b]thiophen-3-yl)-2-phenoxyethanone (5 g), acetic acid (23 ml) and concentrated sulphuric acid (6 drops) was heated at 90°–95° C. under nitrogen for 16 hours, then the solvent was removed in vacuo. The residue was partitioned between dichloromethane (120 ml) and 5M aqueous sodium hydroxide solution (60 ml), then the aqueous phase was separated and washed with dichloromethane (60 ml). The combined dichloromethane solutions were washed with water (4×50 ml), dried (MgSO$_4$), and the solvent removed in vacuo to leave a red-brown solid (3.55 g). The solid was purified by flash chromatography over silica using a 17:3 mixture of petroleum ether (b.p. 60°–80° C.) and ethyl acetate as eluant. Appropriate fractions were combined, and the solvents were removed in vacuo to leave 3-acetyl-5-fluorobenzo[b]thiophen as an off-white solid (1.8 g), m.p. 90°–92° C.

Phenyltrimethylammonium tribromide (0.4 g) was added in portions under nitrogen over 30 minutes to a stirred solution of 3-acetyl-5-fluorobenzo[b]thiophen (0.2 g) in tetrahydrofuran (4.5 ml), then the mixture was stirred at ambient temperature for 1 hour, allowed to stand at ambient temperature for 18 hours, and filtered. The solvent was removed in vacuo and the residue was combined with the product derived in a similar fashion from 3-acetyl-5-fluorobenzo[b]thiophen (1.5 g). The combined residues were dissolved in ethanol (47 ml), 2-imidazolidinethione (0.9 g) and acetic acid (31 ml) were added, and the mixture was heated under reflux under nitrogen for 20 hours, then allowed to cool to ambient temperature. The resulting precipitate was collected by filtration, washed with ethanol, and dried in vacuo at 60° C to give 3-(5-fluorobenzo[b]thiophen-3-yl)-5,6-dihydroimidazo[2,1-b]thiazole monohydrobromide as a yellow crystalline solid (1.7 g), m.p. 264°–266° C.

EXAMPLE 8

A solution of potassium hydroxide (7.5 g) in a mixture of ethanol (220 ml) and water (55 ml) was added at ambient temperature under nitrogen to a stirred solution of 4-mercaptobenzonitrile (18.0 g; prepared according to the method of S. Krishnamurthy and D. Aimino, J. Org. Chem., 1989, 54, 4458) in a mixture of ethanol (195 ml) and water (12 ml), then the mixture was stirred at ambient temperature for 4.5 hours. A solution of 1-chloro-4-phenoxybut-2-yne (24.1 g; prepared in a similar manner to that described in Example 5) in a mixture of ethanol (195 ml) and water (12 ml) was added dropwise over 1.5 hours, then the mixture was stirred at ambient temperature for 17 hours. The mixture was concentrated in vacuo to remove the ethanol, then the product was diluted with water (150 ml) and extracted into ethyl acetate (2×250 ml). The combined extracts were washed with water (100 ml) and saturated brine (100 ml), dried (MgSO$_4$), and the solvent removed in vacuo to leave 4-(4-phenoxybut-2-ynylthio)benzonitrile as an off-white solid (37.7 g).

A solution of m-chloroperoxybenzoic acid (55% purity; 23.1 g) in chloroform (450 ml) was added dropwise over 2.5 hours to a stirred, ice-cold solution of 4-(4-phenoxybut-2-ynylthio)benzonitrile (22.1 g) in chloroform (190 ml), then the mixture was stirred at ambient temperature for 16 hours and filtered. The filtrate was washed with 5% aqueous sodium carbonate solution (3×230 ml) and water (3×50 ml), then dried (MgSO$_4$), and refiltered.

The filtrate was heated under nitrogen at an external temperature of 80°–85° C. for 1.5 hours, allowed to stand at ambient temperature for 18 hours, heated at an external temperature of 80°–85° C. for 6 hours, and allowed to stand at ambient temperature for 18 hours. The solvent was removed in vacuo to leave crude 2-hydroxy-3-methylene-2-phenoxymethyl-2,3-dihydrobenzo[b]thiophen-5-carbonitrile as an off-white solid (22.7 g).

The solid was dissolved in dichloromethane (380 ml) and the solution was shaken vigorously for a few seconds with 5M aqueous sodium hydroxide solution (230 ml), then the organic solution was separated, washed with water (4×230 ml), and dried (MgSO₄). The solvent was removed in vacuo to leave crude 3-(2-phenoxyacetyl)-2,3-dihydrobenzo[b]thiophen-5-carbonitrile as a pale pink solid (23.1 g).

A mixture of the crude 3-(2-phenoxyacetyl)-2,3-dihydrobenzo[b]thiophen-5-carbonitrile (5 g), acetic acid (20 ml) and concentrated sulphuric acid (5 drops) was heated at 90°–95° C. under nitrogen for 20 hours, then the solvent was removed in vacuo. The residue was partitioned between dichloromethane (100 ml) and 5M aqueous sodium hydroxide solution (60 ml), then the aqueous phase was separated and washed with dichloromethane (50 ml). The combined dichloromethane solutions were washed with water (6×50 ml), dried (MgSO₄), and the solvent removed in vacuo to leave a pink solid (3.5 g). The solid was purified by flash chromatography over silica using a 3:2 mixture of petroleum ether (b.p. 60°–80° C.) and ethyl acetate as eluant. Appropriate fractions were combined, and the solvents were removed in vacuo to leave 3-acetylbenzo[b]thiophen-5-carbonitrile as a pale pink solid (1.5 g).

A solution of phenyltrimethylammonium tribromide (2.8 g) in tetrahydrofuran (5 ml) was added dropwise under nitrogen over 30 minutes to a stirred solution of 3-acetylbenzo[b]thiophen-5-carbonitrile (1.5 g) in tetrahydrofuran (50 ml), then the mixture was stirred at ambient temperature for 2 hours. The resulting solid was collected by filtration and triturated with a hot mixture of ethanol (21 ml) and acetic acid (14 ml). The product was collected by filtration and dried in vacuo to give 3-(bromoacetyl)benzo[b]thiophen-5-carbonitrile as a white solid (1.05 g).

A mixture of 3-(bromoacetyl)benzo[b]thiophen-5-carbonitrile (1.05 g), 2-imidazolidinethione (0.4 g), ethanol (31.5 ml), and acetic acid (21 ml) was heated under reflux under nitrogen for 24 hours, then cooled in ice. The resulting precipitate was collected by filtration, washed with ether, and dried in vacuo at 65° C. to give 3-(5,6-dihydroimidazo[2,1-b]thiazol-3-yl)benzo[b]thiophen-5-carbonitrile monohydrobromide as a white solid (1 g), m.p. 303°–305° C.

EXAMPLE 9

The use of compounds of the present invention in the manufacture of pharmaceutical compositions is illustrated by the following description. In this description the term "active compound" denotes any compound of the invention but particularly any compound which is the final product of one of the preceding Examples.

a) Capsules

In the preparation of capsules, 10 parts by weight of active compound and 240 parts by weight of lactose are de-aggregated and blended. The mixture is filled into hard gelatin capsules, each capsule containing a unit dose of part of a unit dose of active compound.

b) Tablets

|  | Parts by weight |
| --- | --- |
| Active compound | 10 |
| Lactose | 190 |
| Maize starch | 22 |
| Polyvinylpyrrolidone | 10 |
| Magnesium stearate | 3 |

The active compound, the lactose and some of the starch are de-aggregated, blended and the resulting mixture is granulated with a solution of the polyvinyl-pyrrolidone in ethanol. The dry granulate is blended with the magnesium stearate and the rest of the starch. The mixture is then compressed in a tabletting machine to give tablets each containing a unit dose or a part of a unit dose of active compound.

c) Enteric coated tablets

Tablets are prepared by the method described in (b) above. The tablets are enteric coated in a conventional manner using a solution of 20% cellulose acetate phthalate and 3% diethyl phthalate in ethanol:dichloromethane (1:1).

d) Suppsositories

In the preparation of suppositories, 100 parts by weight of active compound is incorporated in 1300 parts by weight of triglyceride suppository base and the mixture formed into suppositories each containing a therapeutically effective amount of active ingredient.

We claim:

1. Compounds of formula I

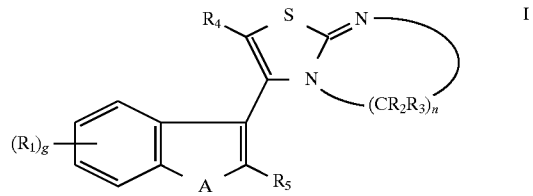

including pharmaceutically acceptable salts thereof in which
A is $S(O)_p$ or O;
p is 0, 1 or 2;
g is 0, 1, 2, 3, or 4;
n is 2 or 3;
$R_1$ is a) halo, b) an alkyl group containing 1 to 3 carbon atoms optionally substituted by one or more halo, c) an alkoxy group containing 1 to 3 carbon atoms optionally substituted by one or more halo, d) an alkylthio group, an alkylsulphinyl group or an alkylsulphonyl group each containing 1 to 3 carbon atoms optionally substituted by one or more halo, e) hydroxy, f) an acyloxy group containing 1 to 3 carbon atoms, g) a hydroxyalkyl group containing 1 to 3 carbon atoms, h) cyano, i) an alkanoyl group containing 1 to 6 carbon atoms, j) an alkoxycarbonyl group containing 2 to 6 carbon atoms, k) a carbamoyl group or a carbamoylmethyl group each optionally N-substituted by one or two alkyl groups each containing 1 to 3 carbon atoms, l) a sulphamoyl or sulphamoylmethyl group each optionally N-substituted by one or two alkyl groups each containing 1 to 3 carbon atoms, or m) an amino group optionally substituted by one or two alkyl groups each containing 1 to 3 carbon atoms; $R_1$ being the same or different when g is 2, 3 or 4;
$R_2$, $R_3$ and $R_4$ independently are H or an alkyl group containing 1 to 3 carbon atoms optionally substituted by one or more halo; and
$R_5$ is a) halo, b) an alkyl group containing 1 to 3 carbon atoms optionally substituted by one or more halo, c) an alkoxy group containing 1 to 3 carbon atoms optionally substituted by one or more halo, d) an alkylthio group, an alkylsulphinyl group or an alkylsulphonyl group each containing 1 to 3 carbon atoms optionally substituted by one or more halo, e) hydroxy, f) an acyloxy group containing 1 to 3 carbon atoms, g) a hydroxyalkyl group containing 1 to 3 carbon atoms, h) cyano, i) an alkanoyl group containing 1 to 6 carbon atoms, j)

an alkoxycarbonyl group containing 2 to 6 carbon atoms, k) a carbamoyl group or a carbamoylmethyl group each optionally N-substituted by one or two alkyl groups each containing 1 to 3 carbon atoms, l) a sulphamoyl or sulphamoylmethyl group each optionally N-substituted by one or two alkyl groups each containing 1 to 3 carbon atoms, m) an amino group optionally substituted by one or two alkyl groups each containing 1 to 3 carbon atoms, or n) H.

2. Compounds of formula I as claimed in claim 1 in which A is $S(O)_p$ or O; p is 0, 1 or 2; g is 0, 1, 2, 3 or 4; n is 3; $R_1$ is a) halo, b) an alkyl group containing 1 to 3 carbon atoms optionally substituted by one or more halo, c) an alkoxy group containing 1 to 3 carbon atoms optionally substituted by one or more halo, d) an alkylthio group, an alkylsulphinyl group or an alkylsulphonyl group each containing 1 to 3 carbon atoms optionally substituted by one or more halo, e) hydroxy, f) an acyloxy group containing 1 to 3 carbon atoms, g) a hydroxyalkyl group containing 1 to 3 carbon atoms, h) cyano, i) an alkanoyl group containing 1 to 6 carbon atoms, j) an alkoxycarbonyl group containing 2 to 6 carbon atoms, k) a carbamoyl group or a carbamoylmethyl group each optionally N-substituted by one or two alkyl groups each containing 1 to 3 carbon atoms, l) a sulphamoyl or sulphamoylmethyl group each optionally N-substituted by one or two alkyl groups each containing 1 to 3 carbon atoms, or m) an amino group optionally substituted by one or two alkyl groups each containing 1 to 3 carbon atoms; $R_1$ being the same or different when g is 2, 3 or 4; $R_2$, $R_3$ and $R_4$ independently are H or an alkyl group containing 1 to 3 carbon atoms optionally substituted by one or more halo; and $R_5$ is H, halo, or an alkyl group containing 1 to 3 carbon atoms optionally substituted by one or more halo.

3. Compounds of formula I as claimed in claim 1 in which A is $S(O)_p$; p is 0, 1 or 2; g is 0, 1, 2, 3, or 4; n is 2; $R_1$ is a) halo, b) an alkyl group containing 1 to 3 carbon atoms optionally substituted by one or more halo, c) an alkoxy group containing 1 to 3 carbon atoms optionally substituted by one or more halo, d) an alkylthio group, an alkylsulphinyl group or an alkylsulphonyl group each containing 1 to 3 carbon atoms optionally substituted by one or more halo, e) hydroxy, f) an acyloxy group containing 1 to 3 carbon atoms, g) a hydroxyalkyl group containing 1 to 3 carbon atoms, h) cyano, i) an alkanoyl group containing 1 to 6 carbon atoms, j) an alkoxycarbonyl group containing 2 to 6 carbon atoms, k) a carbamoyl group or a carbamoylmethyl group each optionally N-substituted by one or two alkyl groups each containing 1 to 3 carbon atoms, l) a sulphamoyl or sulphamoylmethyl group each optionally N-substituted by one or two alkyl groups each containing 1 to 3 carbon atoms, or m) an amino group optionally substituted by one or two alkyl groups each containing 1 to 3 carbon atoms; $R_1$ being the same or different when g is 2, 3 or 4; $R_2$, $R_3$ and $R_4$ independently are H or an alkyl group containing 1 to 3 carbon atoms optionally substituted by one or more halo; and $R_5$ is H, halo, or an alkyl group containing 1 to 3 carbon atoms optionally substituted by one or more halo.

4. Compounds of formula I as claimed in claim 1 in which p is 0; g is 0 or 1; $R_1$ is halo, an alkoxy group containing 1 to 3 carbon atoms, or cyano; $R_2$, $R_3$, $R_4$ and $R_5$ are all H; and n is 2.

5. Compounds of formula I as claimed in claim 1 in which A is 0; g is 0, 1, 2, 3, or 4; n is 2; $R_1$ is a) halo, b) an alkyl group containing 1 to 3 carbon atoms optionally substituted by one or more halo, c) an alkoxy group containing 1 to 3 carbon atoms optionally substituted by one or more halo, d) an alkylthio group, an alkylsulphinyl group or an alkylsulphonyl group each containing 1 to 3 carbon atoms optionally substituted by one or more halo, e) hydroxy, f) an acyloxy group containing 1 to 3 carbon atoms, g) a hydroxyalkyl group containing 1 to 3 carbon atoms, h) cyano, i) an alkanoyl group containing 1 to 6 carbon atoms, j) an alkoxycarbonyl group containing 2 to 6 carbon atoms, k) a carbamoyl group or a carbamoylmethyl group each optionally N-substituted by one or two alkyl groups each containing 1 to 3 carbon atoms, l) a sulphamoyl or sulphamoylmethyl group each optionally N-substituted by one or two alkyl groups each containing 1 to 3 carbon atoms, or m) an amino group optionally substituted by one or two alkyl groups each containing 1 to 3 carbon atoms; $R_1$ being the same or different when g is 2, 3 or 4; $R_2$, $R_3$ and $R_4$ independently are H or an alkyl group containing 1 to 3 carbon atoms optionally substituted by one or more halo; and $R_5$ is H, halo, or an alkyl group containing 1 to 3 carbon atoms optionally substituted by one or more halo.

6. Compounds of formula I as claimed in claim 1 in which n is 2; g is 0 or 1; $R_1$ is halo, an alkoxy group containing 1 to 3 carbon atoms, or cyano; $R_2$, $R_3$, $R_4$ and $R_5$ are all H; and n is 2.

7. Compounds of formula I as claimed in claim 1 selected from the group consisting of:

3-(benzo[b]thiophen-3-yl)-5,6-dihydroimidazo[2,1-b]thiazole;

3-(benzo[b]thiophen-3-yl)-6,7-dihydro-5H-thiazolo[3,2-a]pyrimidine;

3-(benzo[b]furan-3-yl)-5,6-dihydroimidazo[2,1-b]thiazole;

3-(benzo[b]furan-3-yl)-6,7-dihydro-5H-thiazolo[3,2-a]pyrimidine;

3-(5-chlorobenzo[b]thiophen-3-yl)-5,6-dihydroimidazo[2,1-b]thiazole;

3-(5-methoxybenzo[b]thiophen-3-yl)-5,6-dihydroimidazo[2,1-b]thiazole;

3-(5-fluorobenzo[b]thiophen-3-yl)-5,6-dihydroimidazo[2,1-b]thiazole;

3-(5,6-dihydroimidazo[2,1-b]thiazol-3-yl)benzo[b]thiophen-5-carbonitrile; or pharmaceutically acceptable salts thereof.

8. The compound of formula I as claimed in claim 1 which is:

3-(benzo[b]thiophen-3-yl)-5,6-dihydroimidazo[2,1-b]thiazole; and pharmaceutically acceptable salts thereof.

9. A pharmaceutical composition comprising a therapeutically effective amount of a compound of formula I as claimed in claim 1 together with a pharmaceutically acceptable diluent or carrier.

10. A method of treating depression, anxiety, psychoses, tardive dyskinesia, obesity, drug addiction, drug abuse, cognitive disorders, Alzheimer's disease, senile dementia, cerebral ischaemia, obsessive-compulsive behaviour, panic attacks, social phobias, eating disorders and anorexia, non-insulin dependent diabetes mellitus, hyperglycaemia, or stress in human beings which comprises the administration of a therapeutically effective amount of a compound of formula I as claimed in claim 1 to a patient in need thereof.

11. Process for the preparation of compounds of formula I, as defined in claim 1, comprising the reaction of a compound of formula III

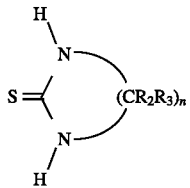

III with a compound of formula IV

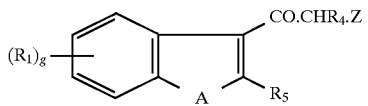

IV at a temperature in the range of 0°–200° C. optionally in the presence of an acid and optionally in the presence of a solvent, the groups R, $R_2$, $R_3$, $R_4$, $R_5$ and A having the meaning set out in claim 1 and Z is a leaving group.

* * * * *

UNITED STATES PATENT AND TRADEMARK OFFICE
CERTIFICATE OF CORRECTION

PATENT NO.: 5,869,492

DATED: February 9, 1999

INVENTOR(S): KERRIGAN et al.

It is certified that error appears in the above-identified patent and that said Letters Patent is hereby corrected as shown below:

On the cover page, the information under "[56] References Cited" should be as follows:

-- FOREIGN PATENT DOCUMENTS

| | | |
|---|---|---|
| 41883/78 | 11/1978 | Australia |
| 94/01437 | 1/1994 | PCT |
| 2400 | 6/1979 | European Pat. Off. |
| 1251729 | 10/1971 | Great Britain |
| 1262893 | 2/1972 | Great Britain |
| 1268848 | 3/1972 | Great Britain |
| 1268849 | 3/1972 | Great Britain |

OTHER PUBLICATIONS

SHARPE et al., J. Med. Chem., 14:10, 1971.--

Signed and Sealed this

Thirteenth Day of February, 2001

*Attest:*

NICHOLAS P. GODICI

*Attesting Officer*     Acting Director of the United States Patent and Trademark Office